(12) United States Patent
Ben et al.

(10) Patent No.: US 7,513,254 B2
(45) Date of Patent: Apr. 7, 2009

(54) RESUSCITATORS

(75) Inventors: Jonathan Kevin Ben, Bushey Heath (GB); Paul James Leslie Bennett, Marston Moretaine (GB)

(73) Assignee: Smiths Group PLC, London (GB)

( * ) Notice: Subject to any disclaimer, the term of this patent is extended or adjusted under 35 U.S.C. 154(b) by 296 days.

(21) Appl. No.: 10/570,351

(22) PCT Filed: Sep. 3, 2004

(86) PCT No.: PCT/GB2004/003788

§ 371 (c)(1),
(2), (4) Date: Mar. 3, 2006

(87) PCT Pub. No.: WO2005/023349

PCT Pub. Date: Mar. 17, 2005

(65) Prior Publication Data

US 2007/0017521 A1 Jan. 25, 2007

(30) Foreign Application Priority Data

Sep. 5, 2003 (GB) .................................. 0320761.0

(51) Int. Cl.
*A61M 11/00* (2006.01)
(52) U.S. Cl. .............................. 128/205.13; 128/205.25
(58) Field of Classification Search ............ 128/205.13, 128/204.26, 204.29, 205.11, 204.18, 204.21, 128/204.25, 204.22, 203.25, 204.24, 205.25

See application file for complete search history.

(56) References Cited

U.S. PATENT DOCUMENTS

| 3,820,566 | A | | 6/1974 | Sundblom et al. |
| 4,060,078 | A | * | 11/1977 | Bird ...................... 128/204.25 |
| 4,127,123 | A | | 11/1978 | Bird |
| 5,520,170 | A | | 5/1996 | Laswick et al. |
| 5,537,999 | A | | 7/1996 | Dearman et al. |
| 5,651,361 | A | | 7/1997 | Dearman et al. |
| 6,055,981 | A | | 5/2000 | Laswick et al. |
| 6,591,835 | B1 | | 7/2003 | Blanch |

FOREIGN PATENT DOCUMENTS

| WO | 92/17235 | | 10/1992 |
| WO | 99/16491 | | 4/1999 |
| WO | 99/47198 | | 9/1999 |
| WO | WO 99/47198 A | * | 9/1999 |

* cited by examiner

*Primary Examiner*—Steven O Douglas
(74) *Attorney, Agent, or Firm*—Louis Woo

(57) ABSTRACT

A gas-powered resuscitator is operable either in a manual mode or an automatic mode. The resuscitator includes an oscillatory timing valve (14) having an outlet (23) connected to a bi-stable valve (25), the operation of which is piloted by a manual valve (16). The outlet (26) of the bi-stable valve (25) connects to the outlet (2) of the resuscitator via a rotatable control (32) and a patient valve (41). The outlet (26) of the bi-stable valve (25) also connects to the control inlet (34) of the timing valve (14). The manual valve (16) has a button (62) that can be pushed down manually in the manual mode or can be held down in the automatic mode by rotating a locking ring (262). The maximum duration of cycles is limited by operation of the timing valve (14), whether the resuscitator is operated manually or automatically.

11 Claims, 3 Drawing Sheets

RESUSCITATORS

FIELD OF THE INVENTION

This invention relates to resuscitators of the kind operable in a first, automatic mode whereby gas is delivered to a patient in a regulated cyclical fashion repeatedly until the mode is terminated and in a second mode whereby a cycle of gas is delivered in response to actuation of a manual member.

BACKGROUND OF THE INVENTION

Resuscitators are used to supply breathing gas to a patient who may not be breathing spontaneously. Portable resuscitators may take the form of a resilient bag that is squeezed manually to supply a volume of air to the patient, the bag refilling with air when it is released so that a new volume of air can be supplied. Alternatively, the resuscitator may be a mechanical device including a tiring valve and various other controls and is connected to an oxygen cylinder, which both provides the breathing gas, or a part of this, and which may also provide the power to drive the components of the resuscitator. Examples of such resuscitators are described in GB 2174760, GB 2174609, EP 343818, EP 342883, EP 343824, GB 2282542, EP 691137, GB 2284159 and GB 2270629. These resuscitators are arranged to supply gas in a cyclic manner to the patient at a rate compatible with normal breathing. The resuscitator usually has some form of manual override so that gas can be provided at a selectively controllable rate such as when the patient is receiving CPR. Existing resuscitators suffer from various problems. For example, where the resuscitator can be operated fully manually, there is a risk that an inexperienced operator could provide inappropriate rates of breathing with possible danger to the patient. Other resuscitators do not allow sufficient flexibility in the administration of gas.

BRIEF SUMMARY OF THE INVENTION

It is an object of the present invention to provide an alternative resuscitator.

According to one aspect of the present invention there is provided a resuscitator of the above-specified kind, characterised in that the resuscitator is arranged such that the cycle is only delivered for so long as the manual member is actuated and that the resuscitator controls the maximum length of the cycle.

The resuscitator may be arranged to deliver repeated ventilation cycles while the manual member is actuated and the resuscitator preferably includes a locking device for holding the manual member in an actuated position. The manual member may include a button that is depressed to actuate a gas delivery cycle, the locking device including a rotatable member operable to retain the button in an actuated position. The rotatable member may extend around the button and be arranged to depress the button when rotated. The rotatable member and the button preferably have cooperating cam formations. The resuscitator preferably includes a first valve controlled by operation of the manual member and a bi-stable valve connected with the first valve to be operated between a fully open or a fully closed position by an output from the first valve, the bi-stable valve controlling supply of gas to the outlet of the resuscitator. The resuscitator preferably includes a timing valve operable to supply cycles of ventilation gas to a patient valve assembly, the output of the timing valve being connected to a manual valve assembly operable by the manual member to prevent or enable flow of ventilation gas to the patient valve assembly, and the output of the manual valve assembly being connected to a control inlet of the timing valve. The resuscitator may include a manually-displaceable control member that is displaceable to alter timing frequency and flow rate simultaneously. The resuscitator may include a gas entrainment device, the manually-displaceable control member being operable also simultaneously to control supply of entrainment gas to the entrainment device. The manually-displaceable control member preferably includes a rotatable member.

According to another aspect of the present invention there is provided a resuscitator including a timing valve operable to supply cycles of ventilation gas to a patient valve assembly, characterised in that the output of the timing valve is connected to a manual valve assembly, which is operable to prevent or enable flow of ventilation gas to the patient valve assembly, and that the outlet of the manual valve assembly is connected to a control inlet of the timing valve.

According to a further aspect of the present invention there is provided a resuscitator including a timing valve, a patient outlet and a gas entrainment device, characterised in that the resuscitator includes a manually-displaceable member displaceable to effect simultaneous control of three separate functions, namely, rate of operation of the tiling valve, supply of gas to the patient outlet and supply of entrainment gas to the entrainment device.

BRIEF DESCRIPTION OF THE DRAWINGS

A resuscitator according to the present invention will now be described, by way of example, with reference to the accompanying drawings, in which.

DETAILED DESCRIPTION OF THE INVENTION

Figure 1:
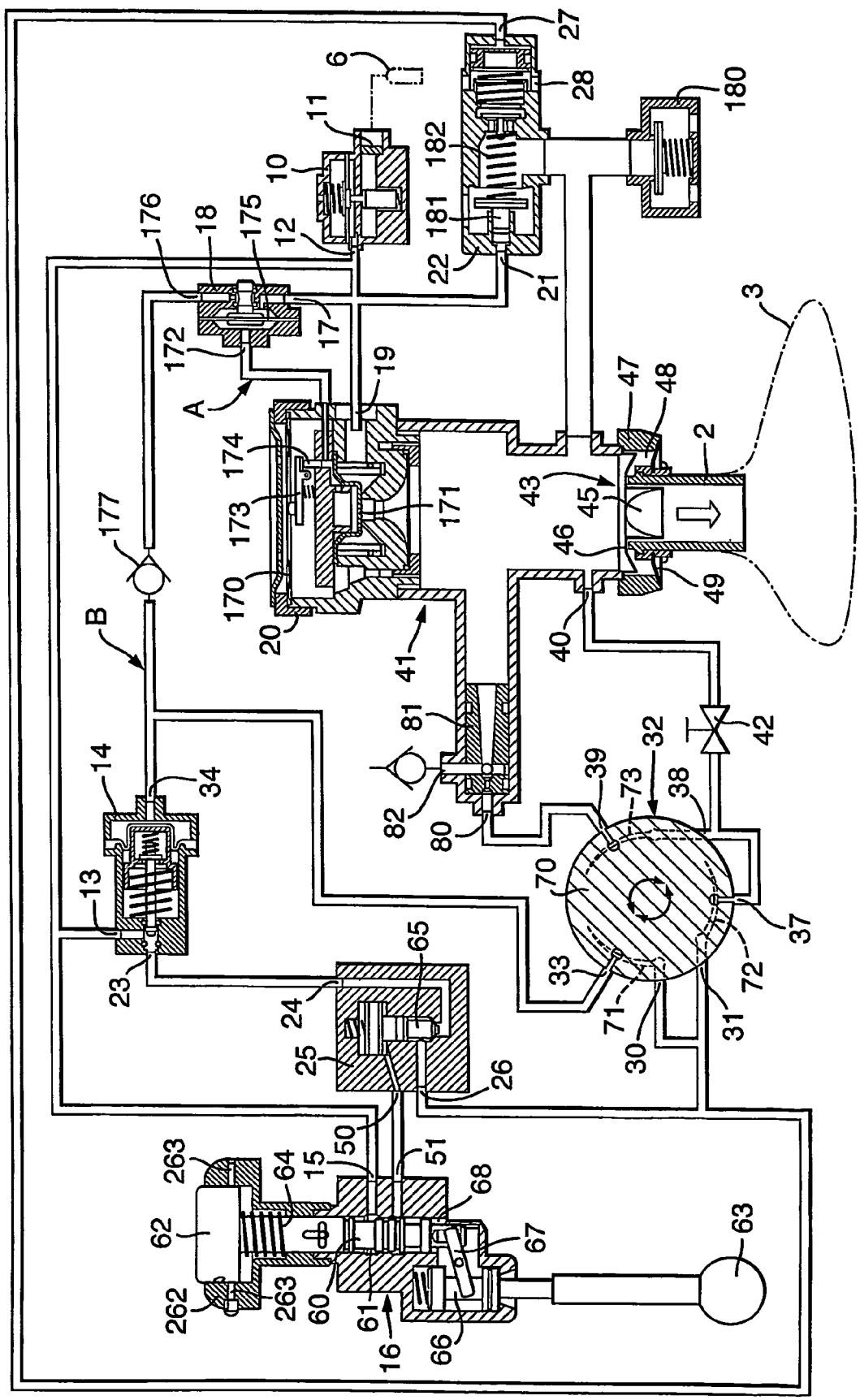
FIG. 1 is a circuit diagram of the resuscitator.
Figure 2:
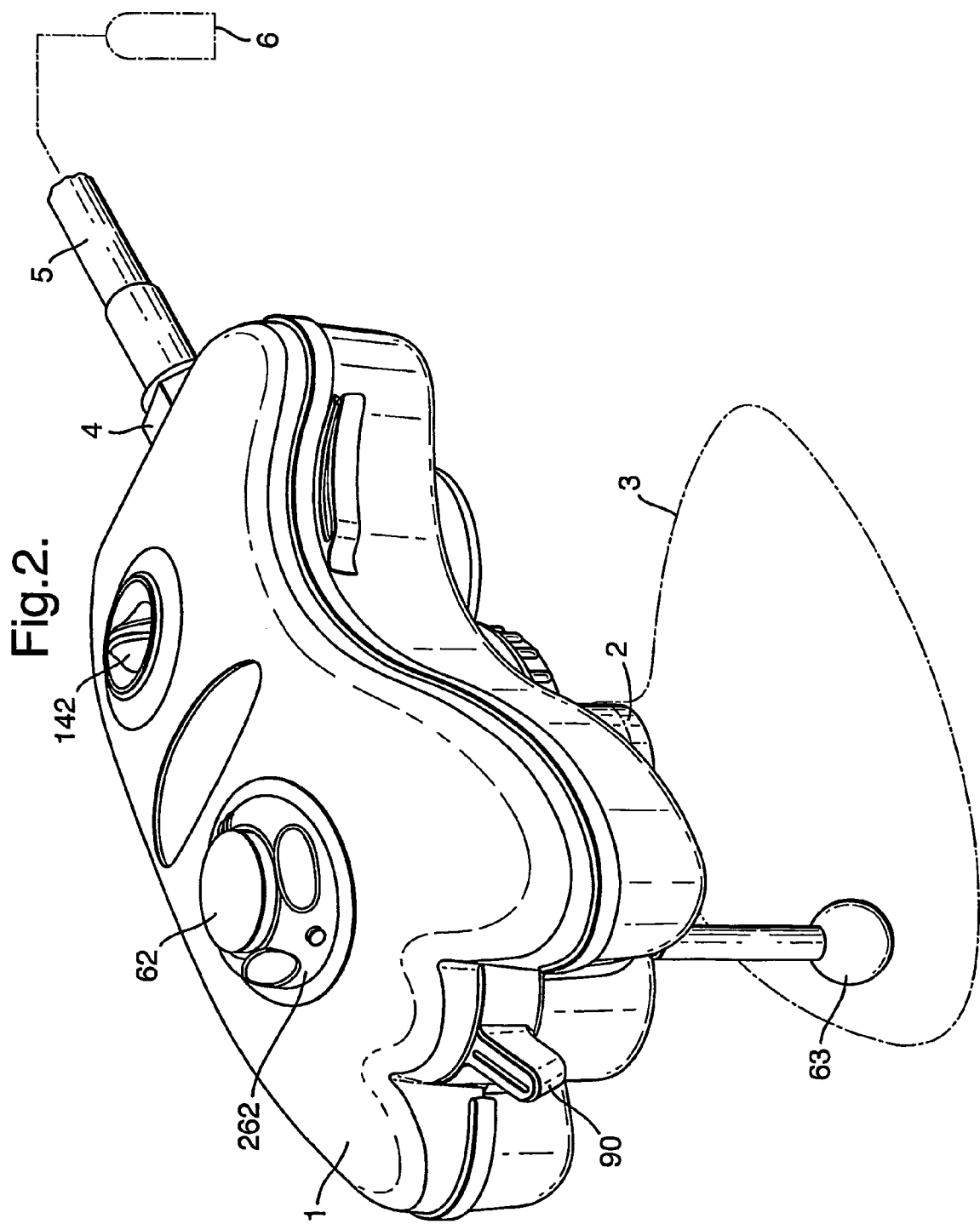
FIG. 2 is a perspective view of the outside of the resuscitator.

With reference first to FIGS. 1 and 2 there is shown the various components of the resuscitator and their interconnections. All the components are contained within a common housing 1, which is sufficiently compact and light to be hand held and connected at its patient outlet 2 directly to a face mask 3. The inlet 4 of the resuscitator is connected via flexible tubing 5 to a source of oxygen, such as a cylinder 6 or, for example, a hospital pipeline, delivering pressure between 40 and 150 psi. This arrangement enables single-handed operation, the same hand holding the face mask 3 and controlling the resuscitator. Alternatively, however, the resuscitator could be located adjacent the oxygen cylinder and its patient outlet connected to a face mask or breathing tube via flexible tubing.

The inlet 4 is provided by a pressure regulator 10 including a filter 11 and an outlet 12, which connects oxygen to various of the other components in the resuscitator. The oxygen splits into five paths. It is supplied to an inlet 13 of an oscillator/timer 14, the inlet 15 of a manual or momentary valve 16, an inlet 17 of a demand detector 18, an inlet 19 of a demand valve 20 and an inlet 21 of a spontaneous breathing valve 22.

Gas supplied to the oscillator/timer 14 flows to its outlet 23 when the oscillator is open or on and from there passes to an inlet 24 of a bi-stable valve 25 the operation of which is controlled by the manual valve 16. The manual valve 16 and the bi-stable valve 25 can be considered together as forming a manual valve assembly. More particularly, operation of the bi-stable valve 25, and hence supply of gas to the patient, is controlled by gas pressure at its pilot inlet 50, which is connected to the outlet 51 of the manual valve 16.

The manual valve 16 includes a spool 60 movable up and down a vertical bore 61 by the action of either a button 62 or a toggle 63. The inlet 15 and outlet 51 open into the bore 61 at locations spaced along its length and the spool 60 has seals that can be positioned to permit or prevent flow of gas from the inlet 15 to the outlet 51 via the bore. In its normal position, as illustrated, a spring 64 urges the button 62, and hence the spool 60, upwards to a position where flow of gas between the inlet 15 and outlet 51 is prevented, so the valve 16 and hence the bi-stable valve 25 is off or closed.

When the button 62 is depressed, the spool 60 moves down and allows pressurised gas at the inlet 15 to pass to the outlet 51 to pilot the piston 65 of the bi-stable valve 25. Alternatively, any movement of the toggle 63 beyond a certain angle, will also pull down the spool 60, via a follower bobbin 66 and crank 67.

When the button 62 or toggle 63 is released, the spool 60 moves upwardly and pressurised gas piloting the piston 65 escapes to atmosphere via a vent 68 at the bottom of the manual valve 16. The manual valve 16 and the bi-stable valve 25 are arranged so that it is not possible to control the ventilation frequency or flow rate by slight operations of either the button 62 or the toggle 63. The output pressure provided by the bi-stable valve 25 is, therefore, either fully on or fully off.

The outlet 26 of the bi-stable valve 25 connects to a pilot inlet 27 of a patient dump valve 28, mounted with the spontaneous breathing valve 22. While the bi-stable valve 25 is open, that is, during the patient inspiratory phase, pressurised gas exiting at the outlet port 26 pilots the patient dump valve 28 at its inlet 27 to cause it to close so that gas cannot escape via the valve. The outlet 26 of the bi-stable valve 25 also connects to two inlets 30 and 31 of a variable restrictor device 32, which is manually adjustable to vary both the tidal volume and the frequency of delivery of gas cycles to the patient.

The restrictor 32 includes a manually-displaceable control member in the form of a rotary plate 70 mechanically coupled with a lever 90 on the casing 1 so that the plate can be rotated through a limited angle by displacing the lever. The restrictor 32 has three tapering grooves one of which 71 connects the inlet 30 with an outlet 33; the second groove 72 connects the inlet 31 with an outlet 37; and the third groove 73 connects an inlet 38 with an outlet 39. Rotating the plate 70 relative movement between the inlets 30, 31 and 38, the outlets 33, 37 and 39 and the grooves 71 to 73 so as to alter the restriction to flow between the respective inlets and outlets. The first groove 71 controls the timing rate of the oscillator/timer 14. The outlet 33 connects to the control or timing inlet 34 of the timer 14 so that rotating the plate 70 such as to produce a higher flow of gas to the timer control inlet increases its frequency of operation, in a manner described in greater detail later.

Gas supplied to the other inlet 31 of the restrictor 32 flows via the second groove 72 to a second outlet 37. The second outlet connects both to the third inlet 38 of the restrictor 32 and to an inlet 40 of a patient valve assembly 41, via an Air Mix/No Air Mix valve 42. The third inlet 38 connects with the third outlet 39 via the third groove 73, which in turn connects to the nozzle inlet 80 of an air entrainment device 81 opening into the patient valve assembly 41.

The second and third grooves 72 and 73 taper in an opposite sense from the first groove 71 so that when the plate 70 is rotated to cause an increased flow at the outlet 33 it causes a reduction in gas flow from the other outlets 37 and 39. Thus, if the user moves the lever 90 to demand an increased frequency of ventilation cycles, this rotates the plate 70 and automatically, simultaneously produces a reduced flow rate or tidal volume of gas. A lower operating frequency is used with children who also require a lower tidal volume.

Instead of the tapering slots 71 to 73 it would be possible for the restrictor to have rows of holes of increasing sizes.

Operation of the Air Mix/No Air Mix valve 42 connected between the outlet 33 and the patient valve assembly 41 is controlled by a rotary knob 142 on the casing 1. The knob 142 can be moved between one of two different positions, marked 100% and 50% respectively. The valve 42 controls whether the patient receives pure oxygen (100%), that is, No Air Mix, or whether this is mixed with air to give an oxygen content of about 50%, that is, Air Mix. When the knob 142 is in the 100% position, the valve 42 is fully open and gas from the outlet 37 flows substantially entirely directly to the inlet 40 of the patient valve assembly 41 because this route presents a lower resistance to flow. If, however, the knob 142 is turned to the 50% position, it turns the valve 42 off completely so that all gas emerging from the outlet 37 now flows via the inlet 38, the groove 73 and the outlet 39 to the inlet 80 of the air entrainment device 81. The high velocity jet of oxygen produced within the entrainment device 81 draws in air from an air inlet 82, which has an oxygen concentration of about 21%. The resultant gas mixture has a nominal oxygen content of 50% and this enters the patient valve assembly 41.

The patient valve assembly 41 has the demand valve 20 at its upper end and a patient valve 43 at its lower end opening into the resuscitator outlet port 2. The patient valve 43 includes a non-return valve 45 of conventional kind, such as described in U.S. Pat. No. 4,774,941. The valve 43 includes a duck-bill valve, arranged to permit flow of gas from the valve assembly 41 to the patient but to prevent flow in the opposite direction into the interior of the assembly. The valve 45 is supported centrally on a flexible diaphragm 46, which bears against the upper end of the outlet port 2. The outlet port 2 is supported coaxially within an outer ring 47 to provide an annular space 48 closed by non-entrainment flap valves 49. Thus, when the patient exhales, the non-return valve 45 closes and the diaphragm 46 lifts off the outlet port 2 to allow the exhaled gas to flow into the annular space 48 and thereby vent to atmosphere via the flap valves 49. The flap valves 49 allow gas to flow out of the annular space 48 but prevent flow in the opposite direction.

Figure 4:
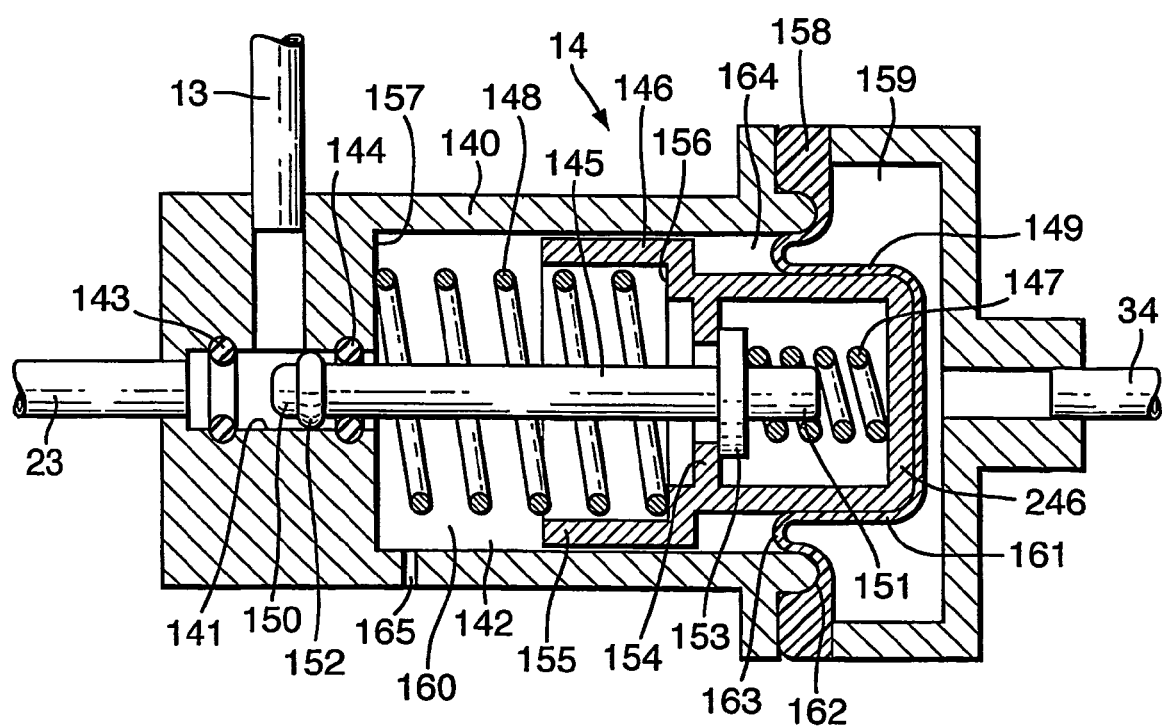
FIG. 4 is a cross-sectional view of the oscillator/timer in greater detail.

Operation of the oscillator/timer 14 will now be described in more detail with reference to FIG. 4. The oscillator/timer 14 has an outer tubular housing 140 into which the control inlet 34 and outlet 23 open axially. The outlet 23 opens into the left-hand end of a relatively small diameter axial bore or passage 141, which opens at its right-hand end into a larger diameter cavity 142. The inlet 13 of the oscillator/timer 14 opens laterally into the bore 141 about midway along its length. Inside the bore 141 there are two O-ring seals 143 and 144, one being located between the inlet 13 and the outlet 23 and the other being located between the inlet 13 and the opening of the bore into the cavity 142. Within the cavity 142 are mounted a sealing rod 145, a cap or piston 146, two helical springs 147 and 148 and a diaphragm 149. The sealing rod 145 is mounted axially and extends with its left-hand end 150 located in the bore 141 and its right-hand end 151 retained within the cap 146. The left-hand end 150 of the rod 145 has an enlarged annular bead 152 set back a short distance from its end and positioned between the two O-rings 143 and 144. The rod 145 extends through the right-hand O-ring 144, which makes a sliding, sealing engagement with the outside of the rod. The right-hand end of the rod 145 has an enlarged flange 153 spaced a short distance from its end, which is engaged on its right-hand side by the left-hand end of the spring 147. The spring 147 extends axially and abuts the inside, closed, right-hand end 246 of the cap 146. The left-hand side of the flange 153 abuts the right-hand side of a flange 154 projecting inwardly of the cap 146 about midway along its length. The left-hand end 155 of the cap 146 is open and enlarged to form an internal shoulder 156 and it is a loose, non-sealing, sliding fit within the cavity 142. The shoulder 156 is contacted by the right-hand end of the second helical spring 148, which is of larger diameter than the first spring 147 and extends axially around the sealing rod 145. The left-hand end of the second spring 148 abuts an end wall 157 at the left-hand end of the cavity 142.

The oscillator/timer 14 is completed by the diaphragm 149, which is made of a flexible, impervious, low stiffness fabric and silicone rubber material. The diaphragm 149 is circular in shape with a thickened circumferential lip 158, which is trapped and sealed between two parts of the housing 1 such that the diaphragm extends transversely of the cavity 142 and seals a rear part 159 of the cavity from a forward part 160. The central part of the diaphragm 149 is moulded with a mesa formation 161 projecting into the rear part 159 of the cavity 142 and closely embracing the external surface of the rear, closed end of the cap 146. Between the mesa formation 161 and the lip 158 the diaphragm 149 curves forwardly around a curved annular lip 162 on the inside of the housing 140 and is formed into a U-shape rolling loop 163 in the annular space 164 between the inside of the housing and the outside of the rear part 246 of the cap 146.

In the natural position of the oscillator/timer 14, the spring 148 pushes the cap 146, and hence the sealing rod 145, rearwardly to a position where the annular bead 152 on the rod is rearwardly, that is, to the right of the opening of the inlet 13 into the bore 141. The passage between the inlet 13 and the outlet 23 is, therefore, unobstructed so that gas can flow through the oscillator/timer 14 and it is on or open. Movement of the sealing rod 145, therefore controls flow of gas along a passage through the oscillator/timer between the inlet 13 and the outlet 23.

When gas pressure is supplied to the control inlet 34, pressure within the rear part 159 of the cavity 142 increases. This causes pressure to be applied to the right-hand side of the diaphragm 149 forcing it against the cap 146 and moving the cap forwardly like a piston, to the left against the action of the spring 148. Air within the left-hand part of the cavity 142 can escape to atmosphere through a small vent hole 165 in the housing 140. As the cap 146 moves to the left, the diaphragm 149 flexes and the loop 163 rolls between the cap and the housing 140, peeling off the outside of the cap and folding against the inside of the housing. Pressure in the bore 141 initially prevents the rod 145 moving so that the spring 147 is compressed as the piston moves forwards. When the rear end 151 of the rod 145 bottoms on the rear end 246 of the piston, the rod is moved forwardly along the bore 141moves until its rear end The spring 147 within the cap 146 bears against the flange 153 on the sealing rod 145 to keep it in contact with the flange 154 on the cap, thereby moving the sealing rod forwardly, along the bore 141. As the rod 145 moves forwardly its annular bead 152 moves to the left of the inlet 13 and the forward end 150 of the rod starts to enter the forward O-ring 143. Pressure across the bead 152 is now equalized and the force of the spring 147 is sufficient to push the rod forwardly so that its bead is in full sealing contact with the left-hand O-ring 143. It can be seen that this blocks flow of gas from the inlet 13 to the outlet 23 and thereby turns the oscillator/timer 14 off. This terminates the inspiratory phase of gas delivery to the patient and starts the expiratory phase.

When the timer/oscillator 14 turns off, all gas in the charging circuit between the outlet 23 of the timer 14 and the inlet 30 of the restrictor 32 escapes to atmosphere through the patient valve assembly 41, either directly via the inlet 40 or via the entrainment device 81. This releases pressure on the patient dump valve 28, allowing it to open, which, in turn, allows the patient circuit pressure to quickly vent to atmosphere via ports in the patient dump valve.

When pressure at the control inlet 34 falls, the spring 148 starts to move the sealing rod 145 back to the open position. Gas in the rear part 159 of the cavity 142 escapes via the inlet 34 back to the restrictor 32 and, in particular, flows to the inlet 30 via the groove 71. The rate of decay of gas pressure is, therefore, determined by the timer setting of the restrictor 32. Once the oscillator/timer 14 is open again a new inspiratory phase starts and the ventilation cycles continue.

It can be seen that the diaphragm 149 provides a complete seal between the two parts 159 and 160 of the cavity 142 and does not rely on moving, wiping seals or this like. Conventional pneumatic pistons use an O-ring to produce a seal. The present construction enables the timing valve 14 to operate with lower friction and stiction forces and hence enables the valve to operate reliably at lower switching pressures. It is important to keep the switching pressures as low as possible in order to ensure that the tidal volume of the first inspiratory breath delivered is not unduly increased. When the manual button 62 is first actuated, the timing valve 14 is open so gas can flow to the patient until pressure at the control inlet 34 has risen to the closing switching pressure. If this pressure were relatively high, gas would flow to the patient for a longer time and the tidal volume delivered could be unduly high. If lower switching pressures are used in conventional, O-ring valves, there is a higher risk of failure especially at very low temperatures of down to −18° C. and especially if the valve is of a small size. The arrangement described can have low friction and stiction forces in a small oscillator over a wide range of temperatures between −18° C. and +50° C.

When using the manual control button 62 or toggle 63, the inspiratory period of the resuscitator lasts for as long as the button is depressed or the toggle is deflected, up to the point of a maximum inspiratory time, as determined by the oscillator/timer 14 and the setting of the variable restrictor 32. With this method of operation it is possible to deliver any volume less than the full tidal volume by releasing the button or lever before complete delivery. By cutting the delivery short, another inspiratory cycle can be delivered proportional to the incomplete volume not delivered and to the time elapsed (the expiratory time) before button 62 is next pressed or the toggle 63 is deflected. It is not possible to deliver two or more full breaths in very close succession, thereby avoiding the possibility of creating stacked breaths and over inflating the patient. If a full 100% tidal volume is delivered, the circuit will lockout until the full expiratory time has passed. After which time, another inspiratory time can be delivered under control.

Figure 3:
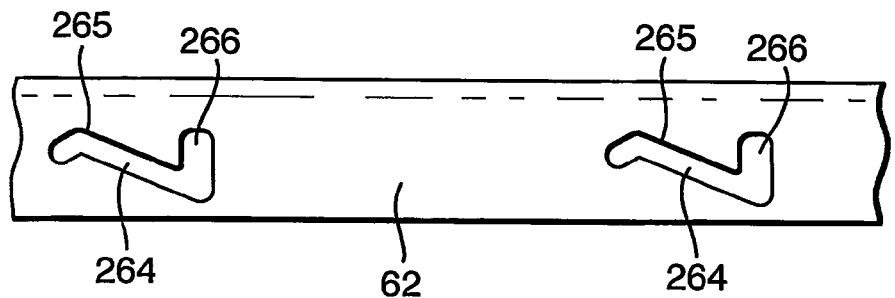
FIG. 3 illustrates cam profiles on the manual control button.

The automatic cycle mode is achieved by holding down the spool 60 by some releasable, mechanical means. In the present example, this is achieved by a rotatable ring 262 surrounding the button 62. When the ring 262 is rotated to its "Automatic" position, two cam pins 263 projecting radially inwardly of the ring engage an inclined portion 264 of two cam profiles 265 (as shown in FIG. 3) formed diametrically opposite one another on the outside of the button 62, thereby pushing down the button. In this way, the button 62 is held in the actuated position and the resuscitator delivers repeated timed ventilation cycles one after the other at a frequency and tidal volume determined by operation of the oscillator/timer 14 and the setting of the restrictor 32. When the ring 262 is rotated back to its "Manual" setting, the cam pins 263 align with vertical sections 266 of the cam profiles 265 so that movement of the button 62 is not impeded.

During any phase of the ventilation cycle, if the patient takes a demand breath, a demand flow will be provided by the demand valve 20. If the demand breath exceeds a pre-set tidal volume and frequency combination, the automatic cycling, if being used, will be temporarily inhibited. During this operation the pressure in the patient circuit drops a few mbar below atmospheric pressure, drawing down a diaphragm 170 in the demand valve 20. Pressure already supplied to the demand valve 20 at the inlet port 19 will have equalized above and below a flexible seal 171 and will have piloted one side of the demand detector 18 via a port 172. Movement of the diaphragm 170 acts on a valve lever 173 and allows pressure above the seal 171 to flow out from a port 174. This action creates a pressure drop across seal 171, which allows gas, at a flow rate demanded by the patient, to enter the patient-circuit. Simultaneously, the drop in pressure above the seal 171 allows a diaphragm 175 of the demand detector 18 to move to the left and opens a path for gas through the demand detector 18 from the inlet 17 to the outlet 176. The gas then passes through a non-return valve 177 to pressurize the timer/oscillator circuit at its control inlet 34. This pressurisation moves the cap 146 and the sealing rod 145 until the path of gas between the inlet 13 and 23 stops, thus, temporarily inhibiting the automatic cycling. When the patient's demand breath has finished, pressure above and below the seal 171 equalizes again and the diaphragm 175 of the demand detector 18 returns back, stopping the path of gas to the outlet 176. At this stage, gas trapped in the oscillator circuit escapes via the normal route and the automatic cycle, in time, will recommence, if in this mode, unless another demand breath is taken. The level of the demand breath dictates the time allowed to charge the oscillator circuit and thus the expiration time available.

In order to limit the maximum patient circuit pressure, the resuscitator further incorporates a pressure relief valve 180 connected to the interior of the patient valve assembly 41. This opens to atmosphere to relieve excess flow when a predetermined pressure is exceeded.

The spontaneous breathing valve 22 includes a piston 181 acted on by a spring 182 to move it to a position where the valve is open to air. The piston 181 is also acted on by gas supply pressure from the regulator 10 such that it is normally held closed. However, if the supply pressure should drop, the valve 22 will open to enable a spontaneously breathing patient to breathe to atmosphere. This provides an alternative breathing path if the supply gas pressure should fall below the input pressure requirements of the demand valve 20.

The circuit may include adjustable restrictors at locations A and B in FIG. 1 by which operation of the resuscitator can be tuned. In particular, a restrictor at position A, between the inlet 172 of the demand detector 18 and the demand valve 20, would be used to control the response of the diaphragm 175 in the demand detector. The other restrictor at position B, between the outlet 176 of the demand detector 18 and the inlet 34 of the timer/oscillator 14, would be used to control the rate at which the timer/oscillator is filled when a patient demand breath has triggered the demand detector.

The invention claimed is:

1. A resuscitator operable in a first, automatic mode whereby gas is delivered to a patient in a regulated cyclical fashion repeatedly until the mode is terminated and in a second mode whereby a cycle of gas is delivered in response to actuation of a manual member, characterized in that the resuscitator is arranged such that the cycle is only delivered for so long as the manual member is actuated and that the resuscitator controls the maximum length of the cycle, and wherein the resuscitator includes a locking device for holding the manual member in an actuated position.

2. A resuscitator according to claim 1, characterized in that the resuscitator is arranged to deliver repeated ventilation cycles while the manual member is actuated.

3. A resuscitator according to claim 1, characterized in that the manual member includes a button that is depressed to actuate a gas delivery cycle, and that the locking device includes a rotatable member operable to retain the button in an actuated position.

4. A resuscitator according to claim 3, characterized in that the rotatable member extends around the button and is arranged to depress the button when rotated.

5. A resuscitator according to claim 4, characterized in that rotatable member and the button have cooperating cam formations.

6. A resuscitator according to claim 1 characterized in that resuscitator includes a first valve controlled by operation of the manual member and a bi-stable valve connected with the first valve to be operated between a fully open or a fully closed position by an output from the first valve, and that the bi-stable valve controls supply of gas to the outlet of the resuscitator.

7. A resuscitator according to claim 1 characterized in that the resuscitator includes a timing valve operable to supply cycles of ventilation gas to a patient valve assembly, that the output of the timing valve is connected to a manual valve assembly operable by the manual member to prevent or enable flow of ventilation gas to the patient valve assembly, and that the output of the manual valve assembly is connected to a control inlet of the timing valve.

8. A resuscitator according to claim 1 characterized in that the resuscitator includes a manually-displaceable control member that is displaceable to alter timing frequency and flow rate simultaneously.

9. A resuscitator according to claim 8, characterized in that the resuscitator includes a gas entrainment device and that the manually-displaceable control member is operable also simultaneously to control the, supply of entrainment gas to the entrainment device.

10. A resuscitator according to claim 8, characterized in that the manually-displaceable control member includes a rotatable member.

11. A resuscitator including a timing valve, a patient outlet and a gas entrainment device, characterized in that the resuscitator includes a manually-displaceable member displaceable between at least three different positions to effect simultaneous variable control of three separate functions, namely, rate of operation of the timing valve, supply of gas to the patient outlet and supply of entrainment gas to the entrainment device, such that the position of the manually-displaceable member determines the values of the said functions.

\* \* \* \* \*